US009341634B2

(12) United States Patent
Maeda et al.

(10) Patent No.: US 9,341,634 B2
(45) Date of Patent: May 17, 2016

(54) METHOD FOR CONTROLLING POST-OPERATIVE SEPSIS INFECTION BY ADMINISTERING ADIPONECTIN

(71) Applicants: Kazuhisa Maeda, Takaishi (JP); Hiroshi Yamamoto, Otsu (JP)

(72) Inventors: Kazuhisa Maeda, Takaishi (JP); Hiroshi Yamamoto, Otsu (JP)

( * ) Notice: Subject to any disclaimer, the term of this patent is extended or adjusted under 35 U.S.C. 154(b) by 31 days.

(21) Appl. No.: 13/890,697

(22) Filed: May 9, 2013

(65) Prior Publication Data

US 2013/0302833 A1 Nov. 14, 2013

Related U.S. Application Data

(63) Continuation of application No. 11/547,169, filed as application No. PCT/JP2005/006395 on Mar. 31, 2005, now abandoned.

(30) Foreign Application Priority Data

Mar. 31, 2004 (JP) ................................ 2004-134823
Mar. 31, 2004 (JP) ................................ 2004-134824

(51) Int. Cl.
*A61K 38/22* (2006.01)
*G01N 33/74* (2006.01)

(52) U.S. Cl.
CPC ............ *G01N 33/74* (2013.01); *A61K 38/2264* (2013.01)

(58) Field of Classification Search
CPC ............................. G01N 33/74; A61K 38/22
USPC ......................................... 435/7.92; 436/501
See application file for complete search history.

(56) References Cited

U.S. PATENT DOCUMENTS

| 7,067,634 | B2 | 6/2006 | Tomita et al. |
| 7,435,551 | B2 | 10/2008 | Tomita et al. |
| 2005/0048565 | A1 | 3/2005 | Tomita et al. |
| 2005/0266506 | A1 | 12/2005 | Tomita et al. |
| 2008/0139468 | A1 | 6/2008 | Maeda et al. |

FOREIGN PATENT DOCUMENTS

| DE | 4237502 | 5/1994 |
| EP | 1426764 | 6/2004 |
| JP | 3018186 | 7/2000 |
| WO | 01/51645 | 7/2001 |
| WO | 03/016906 | 2/2003 |
| WO | 03/062275 | 7/2003 |
| WO | 2004/022596 | 3/2004 |

OTHER PUBLICATIONS

Giugliano et al. "Effect of liposuction on insulin resistance and vascular inflammatory markers in obese women" *Br. J. Plastic Surg.* 57:1-7 (Apr. 2004).
Keller et al. "Circulating adiponectin levels during human endotoxaemia" *Clin. Exper. Immunol.* 134:107-110 (Oct. 2003).
Ouchi et al. "Novel modulator for endothelial adhesion molecules. Adipocyte-derived plasma protein adiponectin" *Circulation* 100:2473-2476 (Dec. 1999).
Ouchi et al. "Adipocyte-derived plasma protein, adiponectin, suppresses lipid accumulation and class A scavenger receptor expression in human monocyte-derived macrophages" *Circulation* 103:1057-1063 (Feb. 2001).
Peake et al. "Human adiponectin binds to bacterial lipopolysaccharide" *Biochem. Biophys. Res. Comm.* 341:108-115 (Mar. 2006).
Tanowitz et al, "Role of the adipocyte in Trypanosoma cruzi infection" *Am. J. Tropical Med. Hygiene* 69:289 Supplement (Sep. 2003) and $52^{nd}$ Annual Meeting of the American Society of Tropical Medicine and Hygiene; Philadelphia, PA, Dec. 3-7, 2003.
Tsuchihashi et al. "Circulation concentrations of adiponectin, an endogenous lipopolysaccharide neutralizing protein, decrease in Rats with polymicrobial sepsis" *J. Surgical Res.* 134:348-353 (Aug. 2006).
Yokota "Shibo saibo o sansei suru adiponectin to macrophage kino (translation: Modulation of macrophage functions by adiponectin, adipocyte-derived plasma protein)" *Clin. Immunol.* 34:584-590 (2000).
Yokota et al. "Adiponectin, a new member of the family of soluble defense collagens, negatively regulates the growth of myelomonocytic progenitors and the functions of macrophages" *Blood* 96:1723-1732 (Sep. 2000).
Int'l Search Report for PCT/JP2005/006395, one page, dated Sep. 13, 2005.
International Preliminary Report on Patentability for PCT/JP2005/006395, six pages, dated Oct. 19, 2006.
Supplementary Search Report for EP 05727482.1, seven pages, dated Apr. 21, 2008.
Extended Search Report for EP 10185392.7, nine pages, dated Jan. 17, 2011.

*Primary Examiner* — Gyan Chandra
(74) *Attorney, Agent, or Firm* — Nixon & Vanderhye PC

(57) ABSTRACT

Physical condition under stress can be controlled by using adiponectin in blood as a stress marker and measuring a level thereof. Moreover, endotoxin activity can be inhibited by using adiponectin.

2 Claims, 3 Drawing Sheets

Adiponectin (ratio of immediately after surgery/before surgery)

METHOD FOR CONTROLLING POST-OPERATIVE SEPSIS INFECTION BY ADMINISTERING ADIPONECTIN

This application is a continuation of application Ser. No. 11/547,169, filed Feb. 20, 2008, now pending; which is the U.S. national stage under 35 U.S.C. 371 of Application No. PCT/JP2005/006395, filed Mar. 31, 2005; the entire contents of which are incorporated by reference in this application.

TECHNICAL FIELD

The present invention relates to a method for control of invasion and use of adiponectin in the fields of biology, medicine, and so on.

BACKGROUND ART

With increases in the proportion of population with obesity in recent years, perioperative management for patients with obesity is deemed to become more important in the realm of surgery. In addition to difficulty in performing an operation itself, obesity is often complicated with so-called metabolic syndrome such as arteriosclerosis, hypertension, and diabetes mellitus and has high possibilities of complications including post operative infection. Therefore, obesity is thought to be an important risk factor in operations. However, influences on surgical stress in patients having such a risk and the risk of post operative complications could not be converted previously into numbers. Adiponectin is known to show low levels in patients with multiple risk factor syndrome including patients with obesity. Perioperative adiponectin measurement can determine influences on the surgery of patients with multiple risk factor syndrome.

On the other hand, excessive operative invasion in the perioperative period sometimes results in patients' miserable outcomes. How to control the generation of excessive inflammatory cytokines at an early stage after surgery is important for preventing post operative complications, particularly post operative infection, from occurring. While a start has recently been made at introducing the immediate measurement of cytokines in blood in post operative management, it may be important for a method for control of cytokines to control only excessive reaction and maintain fundamental vital reaction itself. It is considered that the more detailed control of cytokines or custom-made treatment that takes into consideration difference in the reaction of each individual is required in the future. Thus, a more convenient and unerring stress marker has been demanded strongly.

Moreover, studies on endotoxin have been conducted actively in studies in the biological field and treatments and studies in the medical field of recent years. Attention has been given particularly to the activation of the immune system and the action of stimuli to cytokine production. These actions directly have strong involvement in diseases such as sepsis, liver failure, respiratory failure, DIC, and multiple organ failure (MOF), and there has been considerable interest on measures against them for a long time. Besides, it has recently been revealed that chronic endotoxin stimulation and cytokines including TNF-α induced by this stimulation are involved in the conditions of medical diseases including fatty liver and inflammatory bowel disease.

Although several techniques have been developed previously as techniques for neutralization or removal of endotoxin, their own problems have been pointed out. For example, globulin replacement therapy using anti-core polysaccharide LPS immunoglobulin falls short of preventive effect on infection and improvement in death rate attributed to shock. Monoclonal antibody therapy against lipid A also falls short of improvement in death rate attributed to shock. With progresses in antibacterial peptide (CAP18 peptide) therapy found from human neutrophils and further in the analysis of signals via an endotoxin-specific receptor (TLR), the possibility of anti-TLR antibodies as therapeutic drugs for endotoxin shock has been expected. However, none of them has led to clinical application. Moreover, a polymyxin B-adsorbed column, the only thing that is used clinically, employs extracorporeal circulation and as such, presents problems associated with cost efficiency, decreased blood platelets, and so on. Additionally, it was unclear whether the column improves cytokinemia, which essentially constitutes sepsis. As described above, the conventional techniques are not efficient as techniques for neutralization of endotoxin. Thus, the improvement and development thereof have been demanded strongly.

DISCLOSURE OF THE INVENTION

Problems to be Solved by the Invention

The present invention has been achieved for the sake of solving a variety of problems of the conventional techniques as described above. Namely, an object of the present invention is to provide a stress marker on the basis of ideas totally different from the conventional techniques.

Another object of the present invention is to provide an endotoxin-neutralizing agent on the basis of ideas totally different from the conventional techniques.

Means for Solving the Problems

The present inventors have approached studies from various angles for attaining the object and conducted research and development. As a result, the present inventors have found that invasion can be controlled by using adiponectin in blood as a stress marker and measuring a level thereof.

The present inventors have also approached studies from various angles for attaining the object and conducted research and development. As a result, the present inventors have found that human adiponectin is effective for inhibiting endotoxin activity.

The present invention has been completed on the basis of these findings.

Specifically, the present invention provides each of the following inventions:

(1) A method for control of invasion comprising using adiponectin in blood as a stress marker and measuring a level thereof and a ratio of the adiponectin level after stress to the adiponectin level before stress (e.g., a ratio of the adiponectin level after surgery to the adiponectin level before surgery).

(2) A system for control of invasion complying with the method for control of invasion according to (1).

(3) A method for creating a clinical path using the system for control of invasion according to (2) as a subclass.

(4) A method for predicting the manifestation of post operative infection using the system for control of invasion according to (2).

(5) A method for measuring surgical stress in a patient with metabolic syndrome using the system for control of invasion according to (2).

(6) Adiponectin as a stress marker used for sepsis, hypercytokinemia, multiple organ failure, and so on.

(7) Use of adiponectin as a stress marker in control of invasion.

(8) A method for analyzing stress factors, characterized by using adiponectin.

(9) An endotoxin-neutralizing agent, characterized by comprising human adiponectin in an amount effective for inhibiting endotoxin activity.

(10) A treatment method for disease in need of inhibition of endotoxin activity, characterized by directly administering an endotoxin-neutralizing agent comprising human adiponectin into the body.

Advantageous Effects of the Invention

The use of a method for control of physical condition described in the present invention enables unerring control of post operative invasion or invasion during the treatment of sepsis.

The use of an endotoxin-neutralizing agent described in the present invention enables efficient treatment of, for example, sepsis, multiple organ failure (MOF), DIC, respiratory failure (ARDS), liver cirrhosis, fatty liver, liver failure, inflammatory bowel disease, peritonitis, organ transplantation, dialysis, burns, trauma, intravenous hyperalimentation, and serious acute pancreatitis.

BEST MODE FOR CARRYING OUT THE INVENTION

Figure 1:
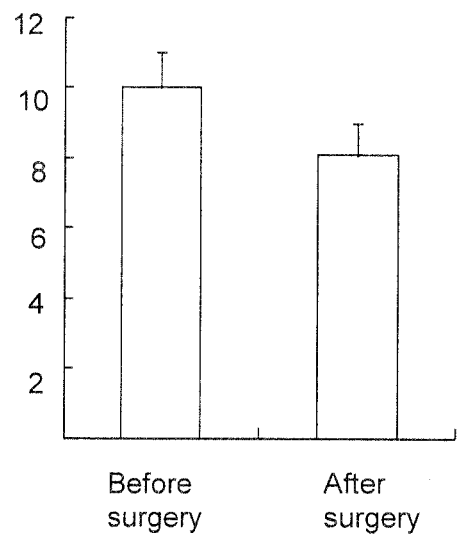
FIG. 1 shows a result of calculating an average value of the concentration of adiponectin in blood after surgery and standard deviation, and is a graph showing that the level of adiponectin in blood is decreased due to operative invasion.

Adiponectin is an endocrine factor specific to adipose tissue cloned by the inventor in Institute for Molecular and Cellular Biology, Osaka University (Maeda K et al.: Biochem Biophys Res Commun 221 (2): 286-9, 1996). It has been revealed that its concentration in blood is decreased in obese individuals, and that even at the same degree of obesity, adiponectin in blood is decreased in arteriosclerotic diseases such as myocardial infarction and angina pectoris and in diabetes mellitus (Maeda K et al.: Annual Review 2004, Internal Secretion, Metabolism, p 15-19). Thus, adiponectin is also considered to be effective for grasping general status before and after surgery in patients with so-called metabolic syndrome such as diabetes mellitus, hypertension, and hyperlipidemia.

The present inventors have recently found that adiponectin directly has the action of inhibiting endotoxin activity. Blood after surgery contains endotoxin at a relatively high concentration. This leads to a decreased concentration of adiponectin having the function of inhibiting the activation of this endotoxin. This is assumed to be because adiponectin is consumed as an endogenous neutralizer acting on endotoxin or because the adiponectin concentration is decreased as a result of hypercytokinemia caused by endotoxin or infection. Thus, it is still further useful for the control of physical condition to pay attention to this adiponectin in monitoring post operative invasion.

Endotoxin is a Gram-negative bacterial cellular component having various bioactivities. Clinically, sepsis (endotoxemia) is quite difficult to treat, and exhibits high fatalities because an effective therapy for the disease is still absent. Recently, the present inventors have created a rat peritonitis model and measured adiponectin, endotoxin, and TNF-α in blood. As a result, the present inventors have found that endotoxin and TNF-α in blood are increased in this peritonitis model as compared with a control group, whereas adiponectin in blood is significantly decreased therein and stands in the mirror-image relationship with TNF-α. This indicates the possibility that adiponectin is consumed as an endogenous neutralizer acting on endotoxin in peritonitis, which is hyperendotoxemia. Since the mutual inhibition of adiponectin and an inflammatory cytokine TNF-α has been reported in vitro, this decrease in adiponectin may be indirect reaction associated with increase in TNF-α activated by endotoxin. In either case, adiponectin or an adiponectin production enhancer may be capable of becoming a breakthrough in sepsis difficult to treat.

Blood after surgery, particularly after abdominal surgery, is considered to contain endotoxin at a relatively high concentration. The present inventors have measured the levels of adiponectin in blood before and after abdominal surgery and found that the level of adiponectin in blood is decreased after surgery as compared with before surgery, and that the rate of this decrease is high in cases complicated with post operative infection disease. The measurement of adiponectin levels before and after surgery can determine the degree of surgical stress and can provide the prediction of post operative infection. Although CRP has frequently been used clinically so far as a marker for post operative acute inflammatory reaction, this marker can hardly reflect changes of actual inflammation in real time. It seems to be still further useful for post operative management mainly composed of measures against infection to pay attention to not only the behaviors of inflammatory cytokines and CRP or rather the behavior of adiponectin serving as an anti-inflammatory cytokine during acute inflammation including operative invasion. This technique is useful for a clinical path that has recently been introduced nationwide in that patients can know how their own treatment schedules are or what stage the treatment is in. Simultaneously, this method is strongly expected as a technique that has a great impact on comprehensive medicine and medical economy. It is also possible to use adiponectin in determining a therapeutic course for the prevention of post operative infection, as in the case of the consideration of the change of a post operative subclass in a clinical path.

The significance of perioperative adiponectin measurement is summarized as described below. In this context, the term "perioperative (period)" means a period before, during, and after an operation or surgery.

(1) The risk of metabolic syndrome that has not been converted previously into numbers can be evaluated.

(2) Decrease in the level of adiponectin in blood after surgery that reflects surgical stress and a rise in inflammatory cytokine TNF-α after surgery serves as an index for surgical stress.

(3) Post operative infection can be predicted with a correlation graph of the level of SLP in blood and adiponectin on 10 days after surgery.

In this context, regarding (3), the preventive administration, of antimicrobial agents after surgery is basically confined to the surgery day and the next day in Europe and America, while they are often administered for several days in Japan. When the patient is suspected of infection, several days are required for obtaining the outcome of bacterial culture, during which the administration of antimicrobial agents are often continued. Currently, several university hospitals have initiated large-scale clinical trials on whether an SLP level measured on the day following surgery can be used as an index for the presence or absence of continuation of administration of antimicrobial agents for the subsequent days. The use of SLP, as described above, has just been started in the prediction of post operative infection. It has been shown this time that the level of SLP in blood on 10 days after surgery correlates with adiponectin, and that adiponectin that reflects surgical stress is also useful for the prediction of perioperative infection. As described above, it is also possible to use adiponectin in determining a therapeutic course for the prevention of post operative infection, as in the case of the consideration of the change of a post operative subclass in a clinical path (approach for process control) from, for example, the measurement of adiponectin levels before and after surgery.

The adiponectin targeted by the present invention is not particularly limited by its type and includes full-length protein forms and globular protein forms. Moreover, an animal from which the adiponectin is derived is not particularly limited. For the purpose of post operative management for a human, human adiponectin is used as a marker.

A method for measuring the marker may be performed according to a standard method, and examples thereof include, but not particularly limited to, a method performing western blotting with a specific antibody and a method using an ELISA kit manufactured by Linco. A sample may be blood itself or blood from which blood corpuscle components have been removed or may further be a concentrate thereof.

The control of invasion shown in the present invention is intended for the prediction and early treatment of post operative infection and the creation of treatment schedules including a subclass in a clinical path. Particularly, it is quite important to convert into numbers, influences on surgical stress in a patient with metabolic syndrome that is considered to increase more and more in number in the future.

For the control of invasion, the concentrations of adiponectin in the blood of an individual to be predicted may be compared before and after surgery. In this context, at least 10% or more, preferably 20% or more, even more preferably 30% or more increase with respect to the concentration value of adiponectin in blood before surgery makes it clear that the individual to be predicted is susceptible to infection, insulin resistance, sepsis, hypercytokinemia, and multiple organ failure attributed to stress.

The human adiponectin is not particularly limited by its type and includes full-length protein forms and globular protein forms. In the present invention, human adiponectin that neutralizes a low concentration (50 pg/ml to 50 ng/ml) of endotoxin is contained at a concentration of 0.1 to 100 µg/ml, preferably at a concentration of 0.5 to 50 µg/ml, more preferably at a concentration of 1 to 10 µg/ml. Adiponectin concentrations of 0.1 µg/ml or lower do not serve as sufficient concentrations in blood. In contrast, adiponectin concentrations of 100 µg/ml or higher are not preferable because they deviate from physiological concentrations in human.

The human adiponectin according to the present invention is used as a preparation in various forms. Specific examples thereof include, but not particularly limited to, injections, suspensions, suppositories, ointment, creams, gels, adhesive skin patches, and inhalants. Particularly, the injections are prepared by dissolving human adiponectin in an appropriate solvent and may be supplemented with a buffer and a preservative.

The neutralizing agent shown in the present invention may also be in a form where human adiponectin has been immobilized. A method for the immobilization is not particularly limited and may be performed with a condensing agent and so on known as a standard method. Moreover, the shape of a carrier on which human adiponectin is adsorbed is not particularly limited, and examples thereof include membranes, fibers, hollow fibers, particulate matters, and nonwoven fabrics.

A pharmaceutical drug as the endotoxin-neutralizing agent shown in the present invention is not particularly limited as long as its efficacy is recognized. Examples thereof include therapeutic drugs for sepsis, multiple organ failure (MOF), DIC, respiratory failure (ARDS), liver cirrhosis, fatty liver, liver failure, inflammatory bowel disease, peritonitis, organ transplantation, dialysis, burns, trauma, intravenous hyperalimentation, and serious acute pancreatitis. Furthermore, the pharmaceutical drug is also expected as an anti-TNF-α drug because human adiponectin inhibits the production and action of TNF-α.

The human adiponectin is not particularly limited by its type and includes full-length protein forms and globular protein forms. In the present invention, human adiponectin that neutralizes a low concentration (50 pg/ml to 50 ng/ml) of endotoxin is contained at a concentration of 0.1 to 100 µg/ml, preferably at a concentration of 0.5 to 50 µg/ml, more preferably at a concentration of 1 to 10 µg/ml. Adiponectin concentrations of 0.1 µg/ml or lower do not serve as sufficient concentrations in blood. In contrast, adiponectin concentrations of 100 µg/ml or higher are not preferable because they deviate from physiological concentrations in human.

The human adiponectin according to the present invention is used as a preparation in various forms. Specific examples thereof include, but not particularly limited to, injections, suspensions, suppositories, ointment, creams, gels, adhesive skin patches, and inhalants. Particularly, the injections are prepared by dissolving human adiponectin in an appropriate solvent and may be supplemented with a buffer and a preservative.

The neutralizing agent shown in the present invention may also be in a form where human adiponectin has been immobilized. A method for the immobilization is not particularly limited and may be performed with a condensing agent and so on known as a standard method. Moreover, the shape of a carrier on which human adiponectin is adsorbed is not particularly limited, and examples thereof include membranes, fibers, hollow fibers, particulate matters, and nonwoven fabrics.

A pharmaceutical drug as the endotoxin-neutralizing agent shown in the present invention is not particularly limited as long as its efficacy is recognized. Examples thereof include therapeutic drugs for sepsis, multiple organ failure (MOF), DIC, respiratory failure (ARDS), liver cirrhosis, fatty liver, liver failure, inflammatory bowel disease, peritonitis, organ transplantation, dialysis, burns, trauma, intravenous hyperalimentation, and serious acute pancreatitis. Furthermore, the pharmaceutical drug is also expected as an anti-TNF-α drug because human adiponectin inhibits the production and action of TNF-α.

EXAMPLES

Hereinafter, the present invention will be described more specifically with reference to Examples. However, the present invention is not intended to be limited to them by any means.

Example 1

The concentrations of adiponectin in blood before and after surgery in 38 cases of abdominal surgery (19 male cases and 19 female cases) were measured according to a standard method to calculate an average value thereof and standard deviation. The obtained results are shown in FIG. 1. This shows that the concentration of adiponectin in blood is decreased due to abdominal surgery. The concentrations of adiponectin in blood before and after surgery were 10±1.0 μg/ml and 8.1±0.9 μg/ml, respectively, and the concentration of adiponectin after surgery was significantly ($p<0.0001$) decreased as compared with before surgery.

Example 2

Figure 2:
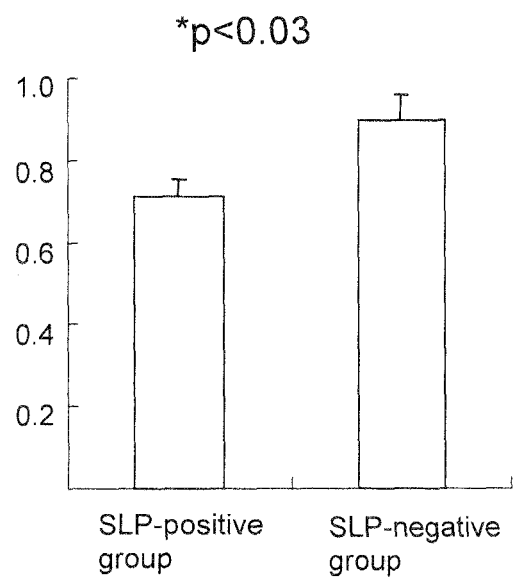
FIG. 2 is a graph showing a result of comparison between a group with infection (positive group for the level of SLP in blood) and a negative group on 10 days after surgery. The graph shows that the adiponectin level is significantly decreased in the SLP-positive group after surgery as compared with before surgery.

The ratio of the concentration of adiponectin in blood after surgery to the concentration of adiponectin in blood before surgery (adiponectin concentration after surgery/adiponectin concentration before surgery) in 38 cases of abdominal surgery was calculated and compared between a positive group and a negative group for the level of SLP in blood on 10 days after surgery. The obtained results are shown in FIG. 2. The ratio was 0.71±0.05 in the SLP level-positive group and 0.90±0.06 in the negative group, and the positive group exhibited the significantly ($p<0.03$) low value. This shows that perioperative infection can be predicted by measuring the concentrations of adiponectin in blood before and immediately after surgery, and that the ratio of the concentration of adiponectin in blood after surgery to the concentration of adiponectin in blood before surgery is useful for the prediction of perioperative infection attributed to abdominal surgery. In this context, the SLP (Silkworm larvae plasma) test is a method for measuring, in blood, the whole of β-glucan (derived from fungi) and peptidoglycan (derived from Gram-positive cocci and Gram-negative bacilli), both of which are bacterial cell wall components, and has previously been shown to reflect bacterial translocation into blood (Document: Crit. Care. Med., 2002).

Example 3

Figure 3:
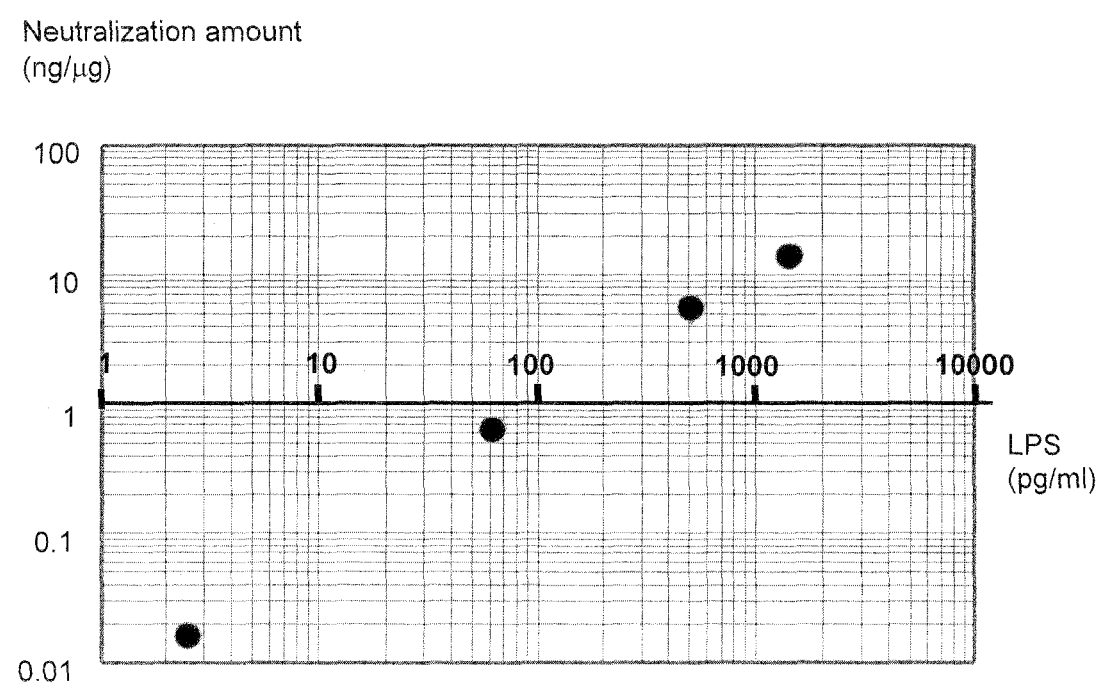
FIG. 3 is a graph showing that a physiological concentration of adiponectin neutralizes a low concentration of LPS and endotoxin.

Aqueous solutions of lipopolysaccharide (*Escherichia coli*-derived lipopolysaccharide, 0111: B4, Catalog No. 4391, manufactured by Sigma) (final concentrations: 50 ng/ml, 5 ng/ml, 500 pg/ml, and 50 pg/ml) were prepared, and each 100-μl aliquot thereof was mixed with 100 μl of distilled water or 100 μl of a solution of 50 μg/ml adiponectin (Techne human recombinant adiponectin, Catalog No. 21065X). After incubation in a thermostat bath at 37° C. for 1 hour, the lipopolysaccharide concentrations were measured by turbidimetric time assay. The obtained results are shown in FIG. 3. This shows that a physiological concentration of adiponectin neutralizes a low concentration of LPS.

Example 4

The concentrations of adiponectin in blood before and after surgery in 30 cases of abdominal surgery (15 cases with post operative infection and 15 cases without post operative infection) were measured. The ratio of the concentration of adiponectin in blood after surgery to the concentration of adiponectin in blood before surgery was 0.68 in the cases with post operative infection and 1.00 in the cases without post operative infection, and this ratio was shown to be significantly high in the cases with post operative infection. This shows that the measurement of adiponectin levels before and after surgery can determine the degree of surgical stress and can provide the prediction of post operative infection.

INDUSTRIAL APPLICABILITY

According to a method described in the present invention, the measurement of adiponectin levels before and after surgery can determine the degree of surgical stress and can provide the prediction of post operative infection. This technique is useful for a clinical path that has recently been introduced by many hospitals in that patients can know how their own treatment schedules are or what stage the treatment is in. Thus, this method is strongly expected as a technique that has a great impact on, for example, comprehensive medicine and medical economy. Thus, the present invention is a quite useful invention in the fields of medicine, biology, and so on.

According to the present invention, endotoxin is neutralized by administering adiponectin. Therefore, endotoxin level can be decreased, and in addition, stimuli by endotoxin to the production of cytokines including TNF-α can be inhibited. Furthermore, the use of anti-TNF-α action of adiponectin enables the treatment of disease conditions caused by high TNF-α levels. This method is strongly expected to be applied to, for example, the neutralization of endotoxin and anti-cytokine (anti-TNF-α) during sepsis. Thus, the present invention is a' quite useful invention in the fields of medicine, biology, and so on.

The invention claimed is:

1. A method for control of post-operative infection, comprising: (a) measuring adiponectin level in the blood before and after a patient's operation to calculate a ratio of the adiponectin level after operation to the adiponectin level before operation, (b) selecting a patient having said ratio of less than 0.81, and (c) administering a pharmaceutically effective amount of adiponectin to said selected patient to control post-operative infection, wherein the infection is involved in sepsis.

2. The method for control post-operative infection according to claim 1, wherein the operation is a transplantation treatment.

* * * * *